United States Patent
Agara Venkatesha Rao et al.

(10) Patent No.: US 10,861,226 B2
(45) Date of Patent: *Dec. 8, 2020

(54) VOLUME SURFACE GENERATOR USING WAVE VECTORS

(71) Applicants: Krishna Prasad Agara Venkatesha Rao, Bengaluru (IN); Srinidhi Srinivasa, Bengaluru (IN)

(72) Inventors: Krishna Prasad Agara Venkatesha Rao, Bengaluru (IN); Srinidhi Srinivasa, Bengaluru (IN)

(73) Assignee: Ricoh Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,113

(22) Filed: Mar. 7, 2019

(65) Prior Publication Data

US 2020/0286280 A1    Sep. 10, 2020

(51) Int. Cl.
*G06T 17/00*     (2006.01)
*G06T 15/08*     (2011.01)
*A61B 5/055*     (2006.01)

(52) U.S. Cl.
CPC ........... *G06T 17/00* (2013.01); *A61B 5/055* (2013.01); *G06T 15/08* (2013.01); *G06T 2210/21* (2013.01); *G06T 2210/41* (2013.01); *G06T 2210/56* (2013.01)

(58) Field of Classification Search
USPC ...................................................... 345/420
See application file for complete search history.

(56) References Cited

U.S. PATENT DOCUMENTS

| 2008/0123921 | A1  | 5/2008  | Gielen et al. |
| 2011/0190569 | A1  | 8/2011  | Simon et al. |
| 2019/0261860 | A1* | 8/2019  | Culver ................. A61B 5/6803 |
| 2019/0320966 | A1* | 10/2019 | Zhu ....................... A61B 5/4064 |
| 2020/0107725 | A1* | 4/2020  | Tyler .................. G01R 33/4814 |

OTHER PUBLICATIONS

United States Office Action, U.S. Appl. No. 16/296,116, dated May 5, 2020, 44 pages.

* cited by examiner

*Primary Examiner* — Gordon G Liu
(74) *Attorney, Agent, or Firm* — Fenwick & West LLP (57) ABSTRACT

A surface model is generated from a three-dimensional volume model of a person's head. The person's head is modelled as a three-dimensional volume model of loss values (i.e., absorption values). Wave vectors are launched towards the volume model. Each wave vector is characterized by a wavelength and a capture direction (direction of propagation). The launched wave vectors are absorbed by the volume and the point at which they are absorbed (referred to as the intersection point) is determined. The surface model of the person's head is generated from the intersection points of the wave vectors.

20 Claims, 7 Drawing Sheets
(4 of 7 Drawing Sheet(s) Filed in Color)

VOLUME SURFACE GENERATOR USING WAVE VECTORS

BACKGROUND

1. Technical Field

This disclosure relates generally to generating surface models, for example generating surface models of a person's brain or skull from volume data of the head, as may be used in magnetoencephalography (MEG) or other types of encephalography.

2. Description of Related Art

In magnetoencephalography (MEG), the brain's electrical activity causes a magnetic field and this is captured by magnetic field sensors positioned at different locations around the brain. These signals can be analyzed for various purposes, such as diagnosing medical conditions, measuring brain function, and conducting research. MEG is especially well-suited for detecting temporal responses. In one common scenario, the subject undergoes different types of stimuli or performs different types of activity and the resulting MEG signals are reviewed for certain responses. The presence or absence of that response may be an indication of a medical condition. Statistical analysis can also be performed across populations of subjects, for example between groups with and without a medical condition.

In many MEG applications, it is useful to have a surface model of a person's head, for example of the exterior surface of the head, or of the skull or of the brain itself. These can be used to develop a head model for subsequent use in the MEG processing pipeline. However, in many cases, the surface model does not exist initially. Rather, a three-dimensional volume model of the head may exist instead. A common example is magnetic resonance imaging (MRI) scans of a person's head, which may be layered to build a three-dimensional volume model of the head. The surface model is then generated from this three-dimensional volume model.

Conventional approaches are based on representing the three-dimensional volume model as a set of voxels and then using vertex clustering and decimation to reduce the voxels. However, this can be time-consuming, especially the tessellation and mesh generation steps. It also is not easy to speed up this process by using parallelization since the process uses nearest neighbor information. The final result also may not accurately capture curved surfaces, and local features may be badly distorted.

Thus, there is a need for better approaches to generate surface models from three-dimensional volume models, including for MEG applications.

SUMMARY

The present disclosure overcomes the limitations of the prior art by providing a computer-implemented method for generating a surface model from a three-dimensional volume model of a person's head. The person's head is modelled as a three-dimensional volume model of loss values (i.e., absorption values). Wave vectors are launched towards the volume model. Each wave vector is characterized by a wavelength and a capture direction (direction of propagation). The launched wave vectors are absorbed by the volume and the point at which they are absorbed (referred to as the intersection point) is determined. The surface model of the person's head is generated from the set of intersection points from the wave vectors.

Other aspects include components, devices, systems, improvements, methods, processes, applications, computer readable mediums, and other technologies related to any of the above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
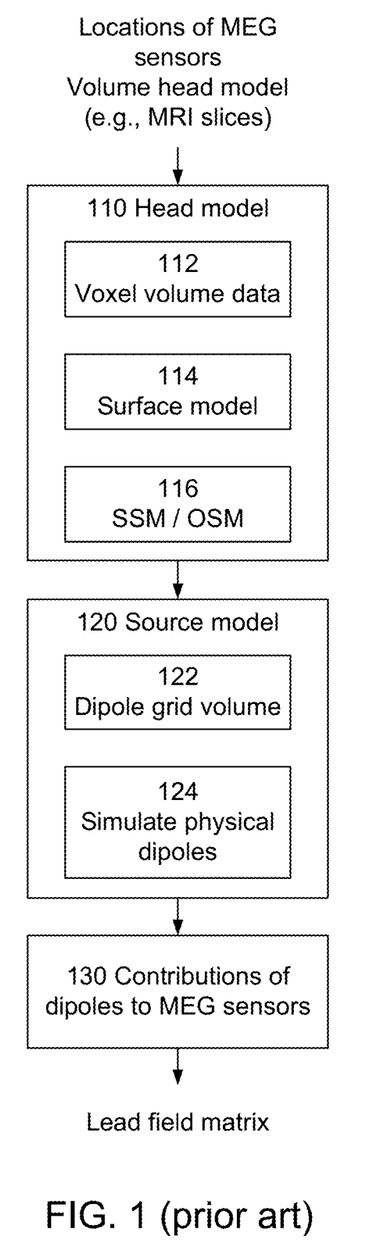
FIG. 1 (prior art) is a flow diagram of a magnetoencephalography (MEG) forward model.

FIG. 1 (prior art) is a flow diagram of a magnetoencephalography (MEG) forward model. In MEG, magnetic field sensors are positioned at different locations around the brain. For example, the patient may position his head inside equipment with an array of MEG sensors or the patient may wear headgear containing an array of MEG sensors. The brain's electrical activity produces a magnetic field and the magnetic field at different locations is measured by the MEG sensors. The process in FIG. 1 is a forward model, which estimates the magnetic field at each MEG sensor for a given pattern of brain activity. This forward model can then be used to solve the inverse problem: Given measurements of the magnetic field at each MEG sensor, estimate the electrical brain activity that produced the measured magnetic fields.

The process has three main steps. A model of the patient's head is generated 110. A model of the sources of magnetic field in the brain is generated 120. The source model 120 is applied to the head model 110 to estimate 130 the magnetic field at each of the MEG sensors.

Figure 2:
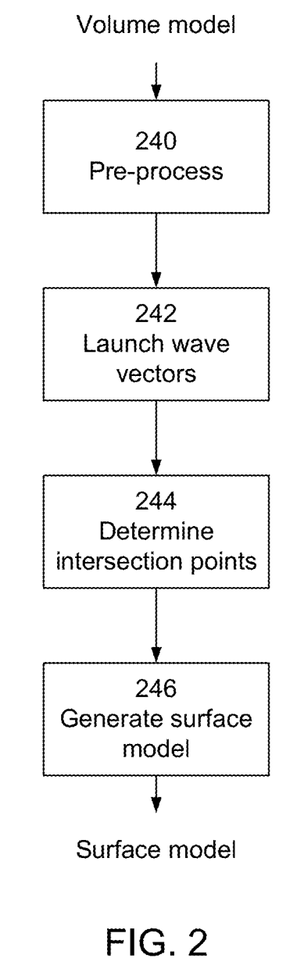
FIG. 2 is a flow diagram for generating a surface model from a three-dimensional volume model of a person's head by launching wave vectors.

In this example, assume that MM slices of the patient's head are available. The head model 110 may be generated as follows. The MRI slices are first assembled into a three-dimensional volume model of the patient's head, for example a three-dimensional model that represents the patient's head as voxels 112. A surface model 114 of the relevant structure is generated from the three-dimensional volume model. In the following examples, a surface model of the patient's brain is generated, but the same techniques may be used to generate surface models of the patient's head or skull. FIG. 2, discussed in more detail below, shows an example in which the volume model is a three-dimensional distribution of loss values (i.e., absorption values), and the surface model 114 is generated by launching wave vectors at the three-dimensional volume model. The surface model 114 is used to generate 116 the head model, for example a single spherical head model (SSM) or an overlapping spherical head model (OSM). In SSM, the patient's brain is represented by a single sphere based on fit to the surface model 114. In OSM, the patient's brain is represented by multiple overlapping spheres, one for each MEG sensor. The spheres are chosen in part to match the local curvature of the brain's surface in the vicinity of the MEG sensor. The SSM/OSM 116 is used to model the propagation of magnetic fields from sources within the brain to the MEG sensors.

The sources within the brain are typically modelled 120 as dipole sources. The synaptic electrical activity in the brain may be modelled as current dipoles. The model includes a distribution 122 of dipoles throughout the volume of the brain. Given a dipole at a certain location of the brain and given the model of the brain volume (e.g., OSM, SSM, other semi-realistic or realistic head model), the magnetic field created by each dipole may be simulated 124. The contributions of all dipoles are aggregated 130 to estimate the total magnetic field at each MEG sensor. This is sometimes referred to as the lead field matrix.

FIG. 2 is a flow diagram for generating a surface model from a three-dimensional volume model of a person's head by launching wave vectors. This is an example implementation of step 114 in FIG. 1. The three-dimensional volume model of the patient's head may be pre-processed 240. Examples of pre-processing include median filtering, averaging, high-pass filtering, anisotropic diffusion, and noise filtering. Wave vectors of different wavelengths are launched 242 from different locations and with different propagation directions (aka capture directions) towards the three-dimensional volume model. The three-dimensional volume model is a distribution of absorption values. The point at which each wave vector is absorbed is determined 244. These points will be referred to as intersection points. The surface model is generated 246 from these intersection points.

Figure 3:
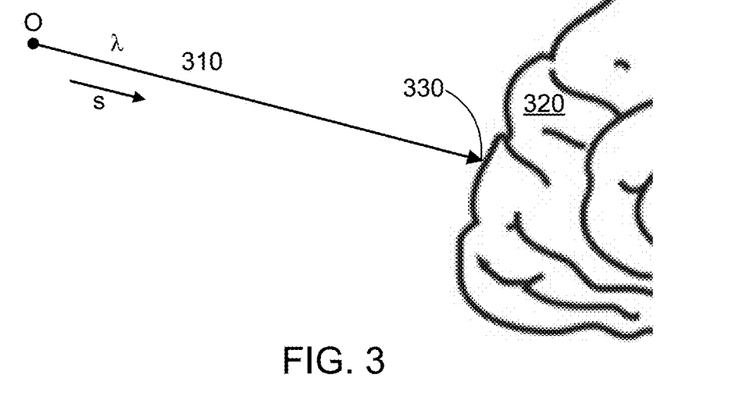
FIG. 3 is a diagram illustrating a wave vector.

FIG. 3 is a diagram illustrating a wave vector 310. The wave vector is defined by an origin O, a capture direction s and a wavelength $\lambda$. The wave vector propagates from the origin O along the capture direction s until it is absorbed by the volume model 320. The absorption point 330 is the intersection point. The location of the intersection point 330 is measured in wavelengths $\lambda$ from the origin O.

The process shown in FIG. 3 does not involve a physical launching of physical waves towards a patient's brain. Rather, terms like "wave vectors are launched" or "wave vectors are transmitted" are phrases that describe a mathematical operation performed on the volume model. There is no actual launching or transmitting of waves towards the physical head or brain of the patient. The wavelength $\lambda$ is analogous to the sampling period of this process. Using larger wavelengths results in a process that is faster to compute but with lower spatial resolution. Using shorter wavelengths results in higher spatial resolution, but requires more computation time. In one approach, multiple wave vectors of different wavelengths are used. For example, wave vectors of longer wavelength may be launched initially to estimate the approximate location of the brain surface, with wave vectors of increasingly shorter wavelengths launched later to refine the estimated location. In this way, the location of the brain surface may be determined with sub-voxel and sub-wavelength accuracy.

In addition, in FIG. 3, the intersection point 330 is shown as the location at which the wave vector 310 strikes the boundary of the brain volume 320. In this figure, the boundary is very well-defined. It starts at a specific location and it transitions instantaneously from non-absorbing to fully absorbing. As the wave vector 310 propagates towards the volume 320, it is not absorbed at all until it hits the boundary and then it is entirely absorbed at a specific point. However, actual volume models may be partially absorbing. The loss values in the volume model may take analog values rather than just a binary value of fully non-absorbing or fully absorbing. In one approach, the point at which the wave vector is considered to be absorbed (i.e., the intersection point) is where the wave vector first encounters loss values in the volume model that are above a certain threshold. In another approach, the intersection point is determined by the cumulative loss value encountered by the wave vector as it propagates. When the cumulative loss value exceeds some threshold, the wave vector is considered to be absorbed.

In addition, the volume model 320 may be a collection of voxels, or a three-dimensional point cloud of irregularly spaced samples, or samples that may or may not align with the wave vector. In these cases, samples of the volume model may be interpolated to determine the loss along the wave vector and the location of the intersection point.

FIG. 3 shows the launching of a single wave vector 310, of a single wavelength, from a single origin, along a single capture direction. To generate the surface model, many wave vectors are launched, using different wavelengths, from different origins and along different capture directions.

In one approach, the wave vectors are organized into wave bundles. Each wave bundle includes many wave vectors with the same wavelength launched along the same capture direction. However, the wave vectors are laterally offset from each other. Thus, there may be an array of wave vectors all launched parallel to but laterally separated from each other. The wave vectors in the wave bundle intersect the volume model at different points, thus providing a surface profile of the brain as viewed from a certain direction. Additional wave bundles launched in the same direction but with different wavelengths can provide greater accuracy and/or reduced computation time.

Figure 4:
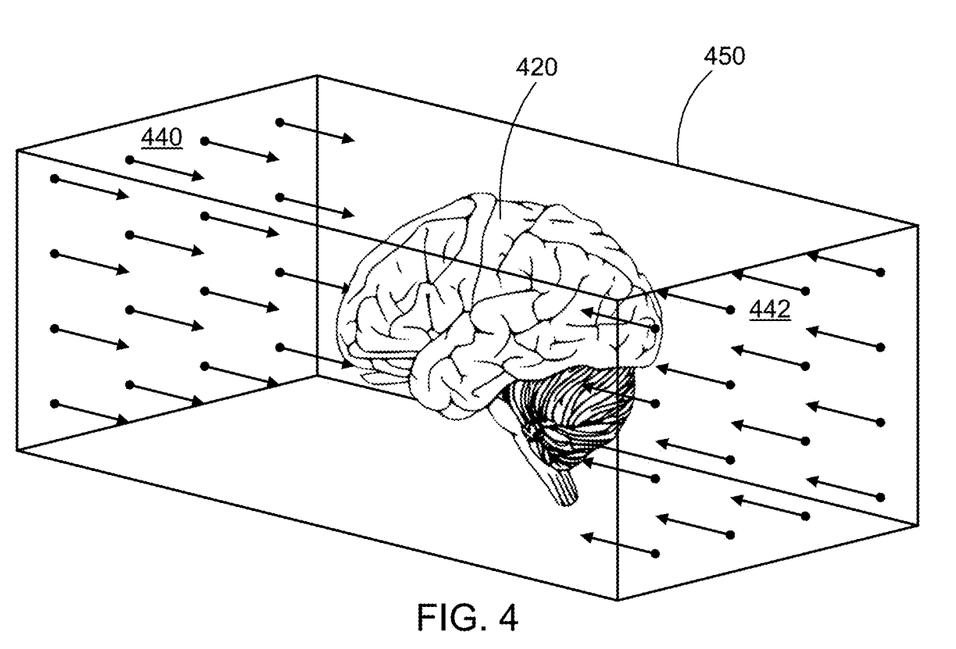
FIG. 4 is a diagram illustrating launching of a wave bundle and its counter-propagating wave bundle towards a three-dimensional volume model.

FIG. 4 is a diagram illustrating the launching of a wave bundle 440 and its counter-propagating wave bundle 442 towards the three-dimensional volume model 420. Wave bundle 440 generates intersections points that define the front surface of the brain. Wave bundle 442 generates intersection points on the back surface of the brain. This can provide a good sampling of the front and back surfaces. However, these two wave bundles propagate along capture directions that are not well suited to profile the top, bottom or sides of the brain. To do so, different capture directions are used.

In one approach, a cuboid 450 encloses the brain volume model 420 and wave bundles are launched from the different faces of the cuboid. FIG. 4 shows the wave bundles launched from the front and back faces of the cuboid 450. Wave bundles may also be launched from the left and right faces, and from the top and bottom faces.

Wave bundles launched in different direction can collectively provide a full 360-degree view of the surface. In one approach, pairs of wave bundles are launched along the sagittal, coronal and axial directions. One wave bundle of each pair is launched in one direction, and the other wave bundle in the pair is launched in the counter-propagating direction. If additional accuracy is desired, additional wave bundles may be launched along the diagonals between these principal directions.

Figure 5:
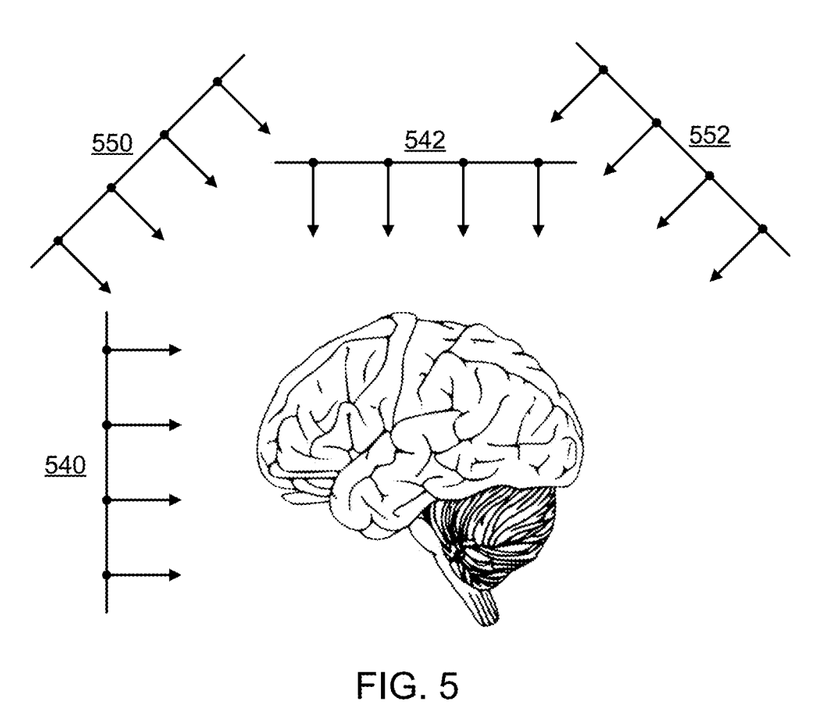
FIG. 5 is a diagram illustrating launching of wave bundles from different capture directions.

FIG. 5 is a diagram illustrating launching of wave bundles from different capture directions. For clarity, the counter-propagating wave bundles are not shown. Wave bundle 540 is launched along the coronal direction (front-back or perpendicular to the coronal plane), and wave bundle 542 is launched along the axial direction (top-bottom or perpendicular to the axial plane). The sagittal direction (right-left or perpendicular to the sagittal plane) is the third principal direction (not shown in FIG. 5). Wave bundles may also be launched along the principal diagonals to these directions. In FIG. 5, wave bundles 550 and 552 are launched along the principal diagonals to the coronal and axial directions.

One advantage of this approach is that the wave vectors and wave bundles may be launched in parallel. The intersection points at which each wave vector is absorbed by the volume model does not depend on other wave vectors. Thus, it may be determined in parallel for different wave vectors and/or wave bundles.

The collection of intersection points from the different wave bundles are consolidated into a single point cloud, which is used as the surface model for the brain. Not all of the intersection points must necessarily be used. In areas where there is a dense sampling of intersection points, they may be culled or combined to reduce the total number of samples in the point cloud. The total number of samples can be adjusted depending on the resolution required for subsequent processing. In one approach, the number of samples is reduced by at least fifty percent, sixty percent or more.

Figure 6A:
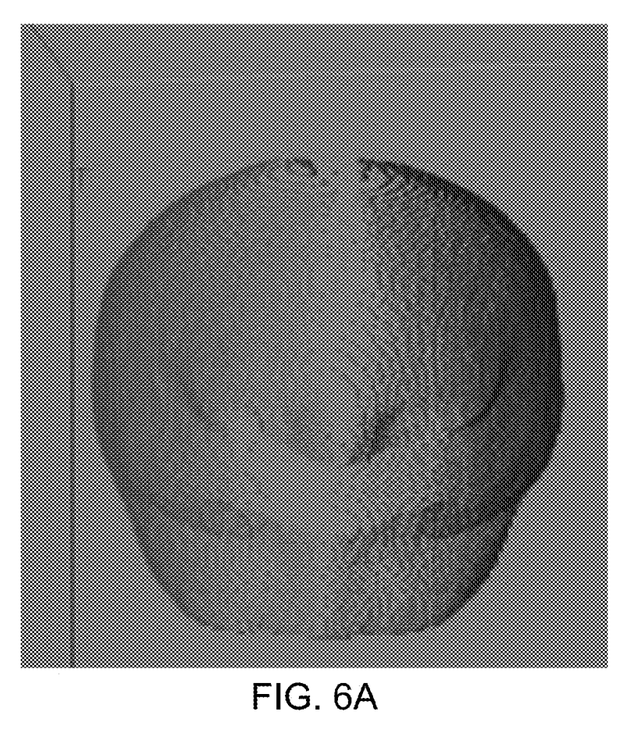
FIGS. 6A-6D show an example of a brain surface model generated by launching wave bundles.
Figure 6B:
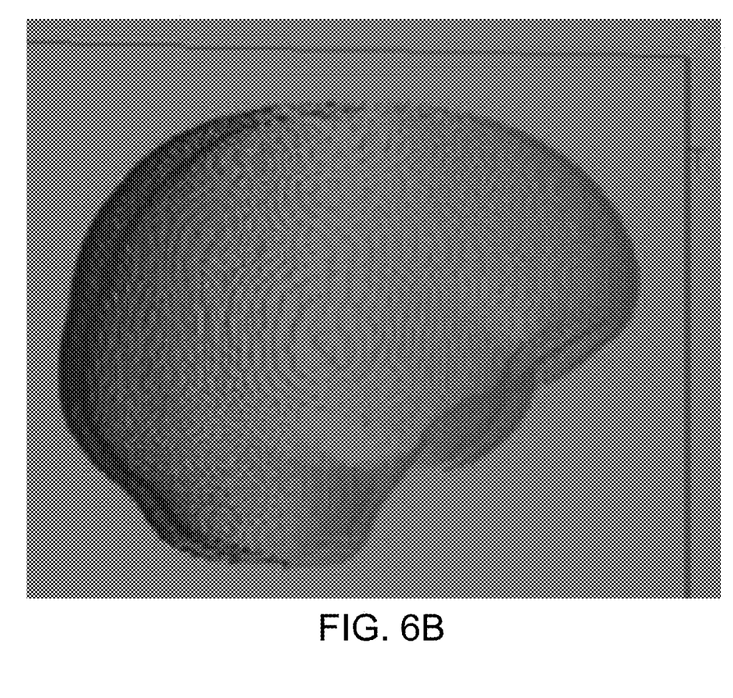
Figure 6C:
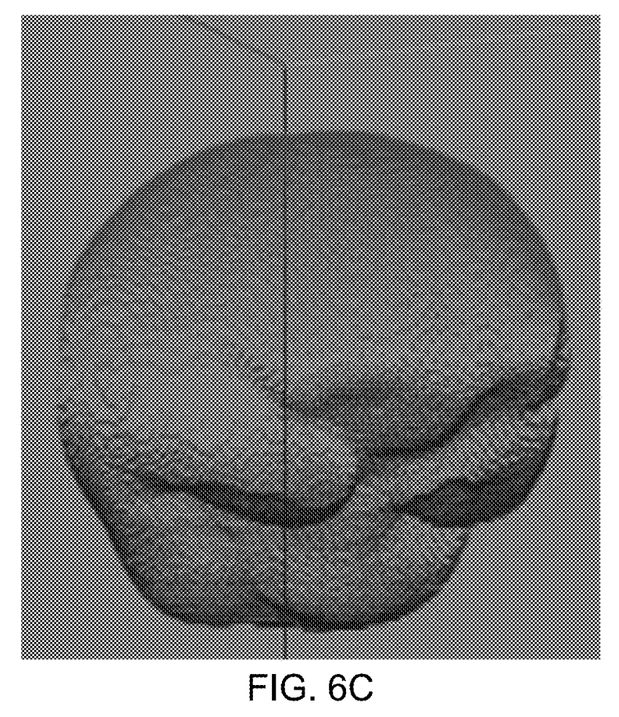
Figure 6D:
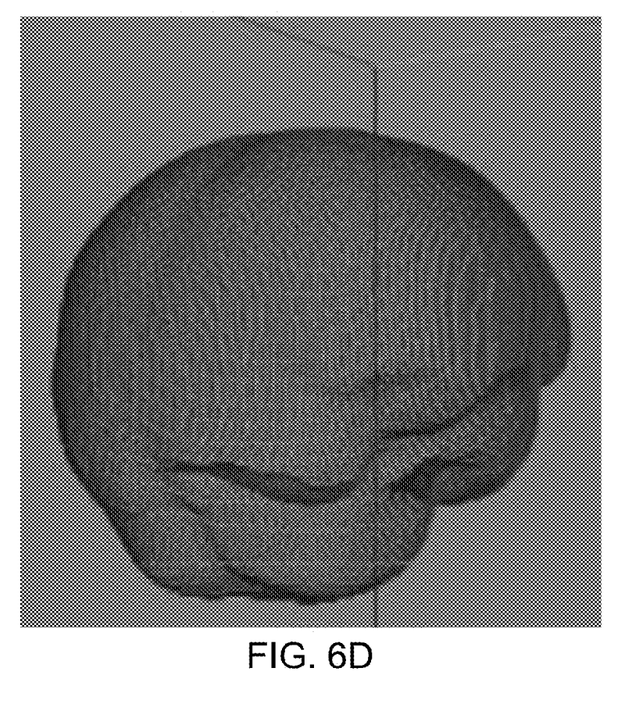

FIGS. 6A-6D show an example of a brain surface model generated by launching wave bundles. FIG. 6A shows the cloud of intersection points generated by wave bundles launched along the sagittal direction. Red and blue indicate points from the two counter-propagating wave bundles. FIG. 6B shows the intersection points from wave bundles launched along the coronal direction. FIG. 6C shows the intersection points from axial wave bundles. FIG. 6D shows the full surface model, which is a point cloud created by combining the point clouds of FIGS. 6A-6C.

Figure 7A:
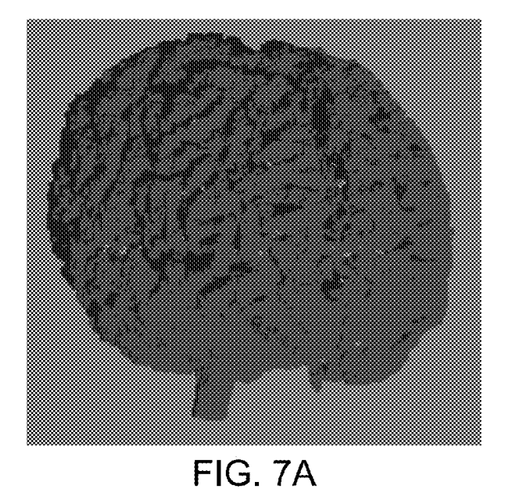
FIGS. 7A-7C show an example of another brain surface model generated by launching wave bundles.
Figure 7B:
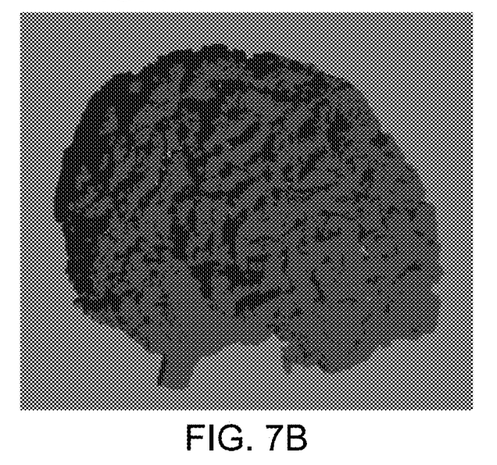
Figure 7C:
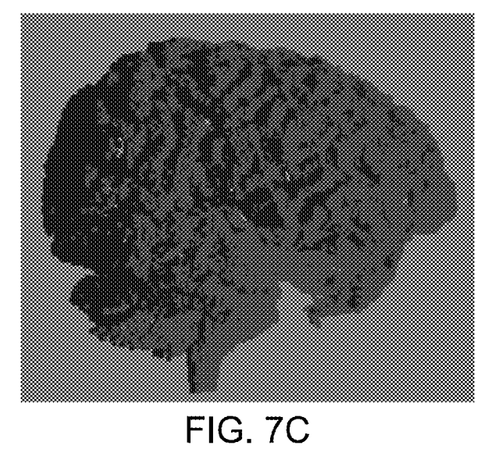

FIGS. 7A-7C show another example. FIGS. 7A-7C rotate from a mostly front view in FIG. 7A, to a front-side view in FIG. 7B to a side view in FIG. 7C. In this example, the surface model captures the more detailed structure of the sulci and gyri of the brain.

In another aspect, the composition of the set of wave vectors is adjustable. For example, the number of wave vectors in each wave bundle, the lateral spacing between wave vectors (including non-uniform spacing), the number of wavelengths and the values of the wavelengths, the number of wave bundles and their capture directions may all be adjusted. Pre-processing (e.g., noise filtering) and post-processing (e.g., fitting a single spherical head model or overlapping spherical head model) may also be adjustable. The number or density of points in the final surface model may also be adjusted.

Figure 8:
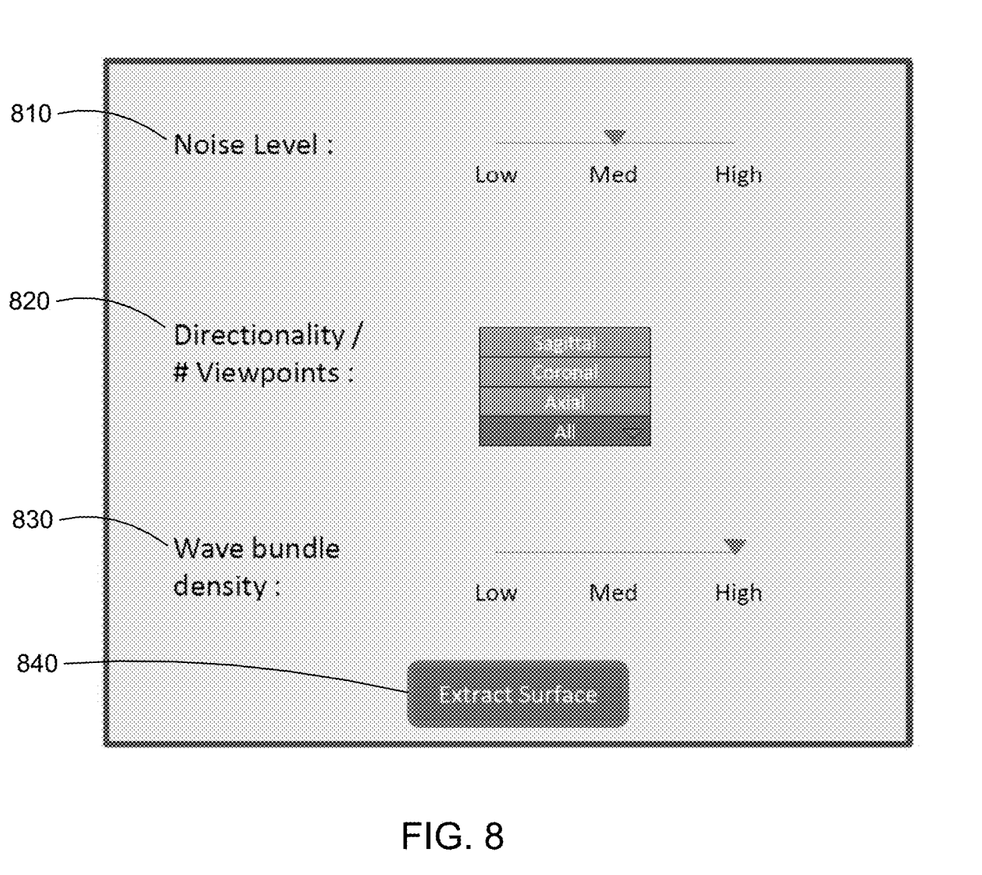
FIG. 8 shows a user interface for adjusting wave bundles.

In one approach, the user makes the adjustments via a user interface. FIG. 8 shows an example user interface. Slider 810 allows the user to select the amount of noise filtering during pre-processing. For example, the user interface may allow selection of the type of filter used for noise reduction or the kernel size. Menu 820 determines which wave bundles are launched. The user interface may also allow selection of the number of wave bundles, and the capture directions for the wave bundles. Slider 830 determines the number of wave vectors per wave bundle, i.e., the lateral offset between wave vectors or the density of the wave vectors. Activating button 840 starts the process using the selected parameters.

In another approach, the adjustments are made dynamically or adaptively, as various wave vectors are launched. The parameters of later launched wave vectors in the set may be adjusted based on the intersection points of previously launched wave vectors in the set. For example, if previously launched wave vectors result in sparse sampling of a certain surface area, later wave vectors may be selected to fill out the sampling of that area.

Although the detailed description contains many specifics, these should not be construed as limiting the scope of the invention but merely as illustrating different examples. It should be appreciated that the scope of the disclosure includes other embodiments not discussed in detail above. For example, the techniques described above may be used in other encephalography applications or other situations where a surface model is generated from a volume model. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments are implemented in computer hardware, firmware, software, and/or combinations thereof. Implementations can be implemented in a computer program product tangibly embodied in a computer-readable storage device for execution by a programmable processor; and method steps can be performed by a programmable processor executing a program of instructions to perform functions by operating on input data and generating output. Embodiments can be implemented advantageously in one or more computer programs that are executable on a programmable computer system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random-access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits), FPGAs and other forms of hardware.

What is claimed is:

1. A method implemented on a computer system, the computer system executing instructions to effect a method for generating a surface model from a three-dimensional volume model of a person's head, the method comprising:
   performing a computer simulation that includes launching a plurality of wave vectors towards the three-dimensional volume model, each wave vector characterized by a wavelength defining a sampling period of the computer simulation and launched along a capture direction, the three-dimensional volume model including a distribution of absorption values;
   determining an intersection point at which each wave vector is absorbed by the three-dimensional volume model using the absorption values; and
   generating a surface model of the person's head from the intersection points.

2. The computer-implemented method of claim 1 wherein the three-dimensional volume model is based on magnetic resonance imaging (MRI) data.

3. The computer-implemented method of claim 1 wherein the surface model of the person's head is a surface model of an exterior of the person's head, a surface model of the person's skull, or a surface model of the person's brain.

4. The computer-implemented method of claim 1 wherein the three-dimensional volume model comprises a three-dimensional point cloud.

5. The computer-implemented method of claim 1 further comprising:
   generating a head mask for the person based on the surface model of the person's head.

6. The computer-implemented method of claim 1 further comprising:
   generating a semi-realistic model for the person based on the surface model of the person's head.

7. The computer-implemented method of claim 1 wherein the wave vectors are organized into wave bundles, each wave bundle includes a plurality of wave vectors with the same wavelength launched along the same capture direction but laterally offset from each other, and the wave bundles include pairs of wave bundles launched along counter-propagating capture directions.

8. The computer-implemented method of claim 7 wherein the wave bundles include wave bundles launched along the sagittal, coronal and axial directions.

9. The computer-implemented method of claim 8 wherein the wave bundles include wave bundles launched along principal diagonal directions between the sagittal, coronal and axial directions.

10. The computer-implemented method of claim 1 wherein the wave vectors are organized into wave bundles, and each wave bundle includes a plurality of wave vectors with the same wavelength launched from a common launch plane along the same capture direction but laterally offset from each other.

11. The computer-implemented method of claim 1 wherein determining the intersection point at which each wave vector is absorbed by the three-dimensional volume model comprises:
   determining where the wave vector first encounters absorption values in the three-dimensional volume model that are above a threshold.

12. The computer-implemented method of claim 1 wherein determining the intersection point at which each wave vector is absorbed by the three-dimensional volume model comprises:
   calculating a cumulative absorption value encountered by the wave vector in the three-dimensional volume model; and
   determining the intersection point at which each wave vector is absorbed by the three-dimensional volume model based on the cumulative absorption value.

13. The computer-implemented method of claim 1 wherein the wave vectors are aligned with samples of the three-dimensional volume model.

14. The computer-implemented method of claim 1 wherein the wave vectors are not aligned with samples of the three-dimensional volume model, and determining the intersection point at which each wave vector is absorbed by the volume model comprises interpolating the samples of the three-dimensional volume model.

15. The computer-implemented method of claim 1 wherein the intersection point is determined with sub-wavelength accuracy.

16. The computer-implemented method of claim 1 wherein generating the surface model from the intersection points comprises:
   consolidating the intersection points into a single point cloud as the surface model.

17. The computer-implemented method of claim 16 wherein consolidating the intersection points into a single point cloud reduces a number of points by at least fifty percent.

18. The computer-implemented method of claim 1 wherein determining the intersection point at which each wave vector is absorbed by the three-dimensional volume model is performed in parallel for different wave vectors.

19. The computer-implemented method of claim 1 wherein the wave vectors are organized into wave bundles, each wave bundle includes a plurality of wave vectors with the same wavelength launched along the same capture direction but laterally offset from each other, and determining the intersection point at which each wave vector is absorbed by the three-dimensional volume model is performed in parallel for different wave vectors within the wave bundle.

20. A non-transitory computer-readable storage medium storing executable computer program instructions for generating a surface model from a three-dimensional volume model of loss values for a person's head, the instructions executable by a computer system and causing the computer system to perform a method comprising:
   performing a computer simulation that includes launching a set of wave vectors towards the three-dimensional volume model, each wave vector characterized by a wavelength defining a sampling period of the computer simulation and launched along a capture direction, the three-dimensional volume model including a distribution of absorption values;
   determining an intersection point of each wave vector with a surface of the three-dimensional volume model using the absorption values; and
   generating a surface model of the person's head from the intersection points.

* * * * *